United States Patent
Mao et al.

(10) Patent No.: US 11,499,951 B2
(45) Date of Patent: Nov. 15, 2022

(54) SYSTEMS AND METHODS FOR FAILURE MODE DETECTION IN PROCESS CHROMATOGRAPHY

(71) Applicant: Regeneron Pharmaceuticals, Inc., Tarrytown, NY (US)

(72) Inventors: Nathan L. Mao, Cohoes, NY (US); Scott Carver, Wynantskill, NY (US); Bernhard Schilling, Hudson, NY (US); Eric Shierly, Castleton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 64 days.

(21) Appl. No.: 16/275,467

(22) Filed: Feb. 14, 2019

(65) Prior Publication Data

US 2019/0248850 A1 Aug. 15, 2019

Related U.S. Application Data (60) Provisional application No. 62/631,167, filed on Feb. 15, 2018.

(51) Int. Cl.

| | |
|---|---|
| *G01N 30/88* | (2006.01) |
| *G01N 30/86* | (2006.01) |
| *G01N 30/74* | (2006.01) |
| *B01D 15/42* | (2006.01) |
| *B01D 15/38* | (2006.01) |
| *C07K 1/16* | (2006.01) |
| *C07K 14/475* | (2006.01) |
| *G01N 30/56* | (2006.01) |
| *B01D 15/36* | (2006.01) |
| *G01N 30/02* | (2006.01) |
| *B01D 15/20* | (2006.01) |
| *B01D 15/32* | (2006.01) |

(52) U.S. Cl.
CPC ......... *G01N 30/88* (2013.01); *B01D 15/3804* (2013.01); *B01D 15/424* (2013.01); *C07K 1/16* (2013.01); *G01N 30/74* (2013.01); *G01N 30/8651* (2013.01); *G01N 30/8675* (2013.01); *B01D 15/206* (2013.01); *B01D 15/327* (2013.01); *B01D 15/363* (2013.01); *C07K 14/475* (2013.01); *G01N 30/56* (2013.01); *G01N 2030/027* (2013.01); *G01N 2030/562* (2013.01); *G01N 2030/889* (2013.01)

(58) Field of Classification Search
CPC ......... G01N 2030/625; G01N 30/8631; G01N 30/8634; G01N 30/8637; G01N 2030/889; G01N 30/88; G01N 30/74; G01N 30/8651; G01N 30/8675; G01N 30/56; G01N 2030/027; G01N 2030/562; B01D 15/3804; B01D 15/424; B01D 15/206; B01D 15/327; B01D 15/363; C07K 1/16; C07K 14/475
See application file for complete search history.

(56) References Cited

U.S. PATENT DOCUMENTS

| | | | |
|---|---|---|---|
| 4,802,981 A | 2/1989 | Kenney et al. | |
| 7,732,216 B2 | 6/2010 | Nochumson et al. | |
| 2004/0249082 A1* | 12/2004 | Zhang | B01J 20/103 525/234 |
| 2006/0096903 A1* | 5/2006 | Holman | G01N 30/56 210/198.2 |
| 2008/0299672 A1 | 12/2008 | Nochumson et al. | |
| 2010/0050737 A1* | 3/2010 | Wolters | G01N 30/8665 73/23.22 |
| 2010/0064770 A1 | 3/2010 | Kawana | |
| 2010/0127860 A1 | 5/2010 | Ganguly et al. | |
| 2010/0260411 A1* | 10/2010 | Aga | G01N 21/8483 382/162 |
| 2011/0205535 A1* | 8/2011 | Soller | A61B 5/145 356/300 |
| 2014/0033793 A1 | 2/2014 | Thorson et al. | |
| 2014/0260509 A1 | 9/2014 | Pohl | |

FOREIGN PATENT DOCUMENTS

| | | |
|---|---|---|
| CN | 102841589 A | 12/2012 |
| EP | 0317114 A1 | 5/1989 |
| JP | H07120451 A | 5/1995 |
| JP | 2006-292446 A | 10/2006 |
| JP | 2011220789 A | 11/2011 |
| TW | 200846905 A | 12/2008 |
| WO | WO 2009/094203 A2 | 7/2009 |
| WO | WO-2011042024 A1 | 4/2011 |

OTHER PUBLICATIONS

Biotek (Application Note, accessed online Jun. 10, 2020, published Feb. 6, 2001; <url: biotek.com/resources/docs/PowerWave200_Nucleic_Acid_Purity_Assessment.pdf>) (Year: 2001).*
Zhou et al. "Combination Therapy of VEGF-Trap and Gemcitabine Results in Improved Anti-Tumor Efficacy in a Mouse Lung Cancer Model" PLOS One, Jul. 2013, vol. 8, Issue 7, p. 1-9 (Year: 2013).*

\* cited by examiner

*Primary Examiner* — Ryan B Huang
(74) *Attorney, Agent, or Firm* — Cooley LLP; Ivor R. Elrifi; Matthew Pavao (57) ABSTRACT

The disclosure provides systems and methods useful for predicting or detecting a malfunction in a chromatography process in real-time. In some embodiments, the disclosure provides systems and methods for detecting an atypical profile in a process chromatogram in ion-exchange chromatography of a biologic product.

31 Claims, 8 Drawing Sheets

SYSTEMS AND METHODS FOR FAILURE MODE DETECTION IN PROCESS CHROMATOGRAPHY

RELATED APPLICATIONS

This application claims the benefit of U.S. Ser. No. 62/631,167, filed on Feb. 15, 2018, the contents of which are incorporated by reference in their entirety herein.

FIELD OF THE INVENTION

The present disclosure relates generally to purification methods for biologic products, including the real-time detection of errors in a chromatography process.

BACKGROUND OF THE INVENTION

A successful timely identification of failure mode in a protein chromatography operation can be challenging not only because the failure mode is specific to each unit operation associated with a program but also because an automatic detection method is not readily available. This is particularly true with large-scale manufacturing. Thus, there is a long-felt yet unmet need for a system and method of in-process, scalable, failure mode detection. The disclosure provides such a novel system and method to address and solve this need.

SUMMARY OF THE INVENTION

The disclosure provides systems and methods for monitoring process chromatograms in an automated or semi-automated fashion. In some embodiments of the methods of the disclosure, a measured absorbance intensity within an integral volume window is compared to a maximum absorbance intensity inferred from at least one reference chromatogram, this measured absorbance intensity is used to identify instability in the chromatography matrix, and by predicting and/or identifying an impending failure, the method improves process performance on any scale. Accordingly, the present disclosure provides methods and devices useful for failure mode detection in a chromatography process.

The disclosure provides a method for predicting or detecting a malfunction in a chromatography process, comprising: (a) generating a reference chromatogram from a chromatography column, (b) generating a process chromatogram from the chromatography column, and (c) detecting an atypical profile in the process chromatogram, wherein the atypical profile indicates a potential or actual malfunction of a chromatography process.

In some embodiments of the methods of the disclosure, the method further comprises (d) generating a warning signal.

In some embodiments of the methods of the disclosure, the method further (e) repacking the chromatography column.

In some embodiments of the methods of the disclosure, the chromatography column is suitable for use in ion exchange chromatography.

In some embodiments of the methods of the disclosure, the chromatography column is suitable for use in affinity chromatography.

In some embodiments of the methods of the disclosure, the chromatography column is suitable for use in hydrophobic interaction chromatography.

In some embodiments of the methods of the disclosure, the potential or actual malfunction of the chromatography process is caused by column deterioration. In some embodiments, the column deterioration comprises column bed fracturing.

In some embodiments of the methods of the disclosure, the atypical profile comprises an additional peak on the process chromatogram when compared to a comparable position on the reference chromatogram. In some embodiments, the additional peak occurs during a washing step in the chromatography process. In some embodiments, the washing step precedes an elution step in the chromatography process. In some embodiments, the additional peak occurring during the washing step and precedes the elution step in the chromatography process.

In some embodiments of the methods of the disclosure, including those wherein the atypical profile comprises an additional peak on the process chromatogram when compared to a comparable position on the reference chromatogram, the magnitude of the additional peak indicates a degree of severity of the potential or actual malfunction of the chromatography process. In some embodiments, an increase in the magnitude of the additional peak indicates an increase in the degree of severity of the potential or actual malfunction of the chromatography process. In some embodiments, the malfunction of the chromatography process induces a loss of separation power of the chromatography column.

In some embodiments of the methods of the disclosure, including those wherein the atypical profile comprises an additional peak on the process chromatogram when compared to a comparable position on the reference chromatogram, the atypical profile comprises at least one peak or at least one indentation on the process chromatogram having a decreased sharpness or a decreased magnitude when compared to a peak or an indentation at a comparable position on the reference chromatogram. In some embodiments, the at least one peak or the at least one indentation on the process chromatogram having a decreased sharpness or a decreased magnitude occurs during the washing step. In some embodiments, the at least one peak or the at least one indentation on the process chromatogram having a decreased sharpness or a decreased magnitude follows the elution step.

In some embodiments of the methods of the disclosure, including those wherein the atypical profile comprises an additional peak on the process chromatogram when compared to a comparable position on the reference chromatogram, the atypical profile comprises a first peak or a first indentation having a decreased sharpness or a decreased magnitude on the process chromatogram when compared to a peak or an indentation at a comparable first position on the reference chromatogram and a second peak or a second indentation having a decreased sharpness or a decreased magnitude on the process chromatogram when compared to a peak or indentation at a comparable second position on the reference chromatogram. In some embodiments, the first peak or the first indentation follows the elution step. In some embodiments, the first peak or the first indentation corresponds to an indentation occurring at a start of a collecting step. In some embodiments, the second peak or the second indentation follows a collection step. In some embodiments, the second peak or the second indentation comprises a strip peak.

In some embodiments of the methods of the disclosure, the process chromatogram comprises a measured absorbance intensity, a maximum absorbance intensity, and an integral volume window. In some embodiments, the atypical profile comprises a measured absorbance intensity that exceeds a maximum absorbance intensity during an integral volume window. In some embodiments, the measured absorbance intensity is determined at a wavelength corresponding to ultraviolet (UV) light. In some embodiments, the measured absorbance intensity is determined at a wavelength of between 260 nanometers (nm) and 280 nm, inclusive of the endpoints. In some embodiments, the measured absorbance intensity is determined at a wavelength of 260 nm, providing an $A_{260}$ value. In some embodiments, the measured absorbance intensity is determined at a wavelength of 280 nm, providing an $A_{280}$ value. In some embodiments, the atypical profile comprises a measured absorbance intensity that exceeds a maximum absorbance intensity during an integral volume window and wherein the maximum absorbance intensity has an $A_{260}$ value or an $A_{280}$ value of at least 0.05. In some embodiments of the methods of the disclosure, a typical profile comprises a measured absorbance intensity that does not exceed a maximum absorbance intensity during an integral volume window and wherein the maximum absorbance intensity has an $A_{260}$ value or an $A_{280}$ value of 0.05 or less.

In some embodiments of the methods of the disclosure, a value of an absorbance intensity of an atypical profile and/or a typical profile is measured during an elution step of a preceding column process. In some embodiments, a value of an absorbance intensity of an atypical profile and/or a typical profile is determined at a wavelength corresponding to ultraviolet (UV) light. In some embodiments, the measured absorbance intensity is determined at a wavelength of between 260 nanometers (nm) and 280 nm, inclusive of the endpoints. In some embodiments, the measured absorbance intensity is determined at a wavelength of 260 nm, providing an $A_{260}$ value. In some embodiments, the measured absorbance intensity is determined at a wavelength of 280 nm, providing an $A_{280}$ value. In some embodiments, a signal is sent following a value indicating an atypical profile, which indicates column deterioration.

In some embodiments of the methods of the disclosure, a value of an absorbance intensity of an atypical profile and/or a typical profile is measured during an elution step of a preceding column process. In some embodiments, a value of an absorbance intensity of an atypical profile and/or a typical profile is determined by assessing a pH level of an eluate during an elution step. In some embodiments, the pH indicated an atypical profile because the pH value is higher than expected from a typical profile. In some embodiments, the pH indicated an atypical profile because the pH value is lower than expected from a typical profile. In some embodiments, a signal is sent following a value indicating an atypical profile, which indicates column deterioration.

In some embodiments of the methods of the disclosure, the integral volume window occurs between 1 L and 5,000 L, inclusive of the endpoints. In some embodiments of the methods of the disclosure, the integral volume window occurs between 1000 L and 3,000 L, inclusive of the endpoints. In some embodiments of the methods of the disclosure, the integral volume window occurs between 1000 L and 2500 L, inclusive of the endpoints. In some embodiments, the integral volume window occurs between 1250 L and 2250 L, inclusive of the endpoints. In some embodiments, the integral volume window occurs between 1600 L and 1800 L, inclusive of the endpoints. In some embodiments of the methods of the disclosure, the integral volume window occurs over a volume of 1 L, 10 L, 100 L, 250 L, 500 L, 1000 L, 1500 L, 2000 L, 2500 L, 3000 L, 4000 L, 5000 L or any number of liters in between.

In some embodiments of the methods of the disclosure, the chromatography column comprises a Q Sepharose anion exchange resin.

In some embodiments of the methods of the disclosure, the step of (a) generating the reference chromatogram comprises (1) contacting a starting composition comprising a plurality of pre-determined analytes and a separation composition comprising a matrix, under conditions sufficient for at least one analyte of the starting composition to reversibly bind to the matrix, wherein the chromatography column comprises the separation composition, to produce an analyte-bound column and a first waste composition; (2) contacting the analyte-bound column of (1) and a washing composition, wherein only the at least one analyte of the starting composition remains bound to the matrix to produce a purified analyte-bound column and a second waste composition; (3) contacting the purified analyte-bound column of (2) and an elution composition, wherein the at least one analyte of the starting composition is released from the matrix into the elution composition to produce an eluted analyte composition; (4) collecting the eluted analyte composition; (5) simultaneously with each of steps (1)-(4), contacting each of the first waste composition, the second waste composition, and the eluted analyte composition with ultraviolet (UV) light, (6) measuring an absorbance of the UV light of each of the first waste composition, the second waste composition, and the eluted analyte composition to produce an absorbance value for each of the first waste composition, the second waste composition, and the eluted analyte composition; and (7) generating a chromatogram by plotting the absorbance value of each of the first waste composition, the second waste composition, and the eluted analyte composition as a function of volume of liquid that traverses the chromatography column.

In some embodiments of the methods of the disclosure, the step of (b) generating the process chromatogram comprises (1) contacting a starting composition comprising a plurality of test analytes and a separation composition comprising a matrix, under conditions sufficient for at least one analyte of the starting composition to reversibly bind to the matrix, wherein the chromatography column comprises the separation composition, to produce an analyte-bound column and a first waste composition; (2) contacting the analyte-bound column of (1) and a washing composition, wherein only the at least one analyte of the starting composition remains bound to the matrix to produce a purified analyte-bound column and a second waste composition; (3) contacting the purified analyte-bound column of (2) and an elution composition, wherein the at least one analyte of the starting composition is released from the matrix into the elution composition to produce an eluted analyte composition; (4) collecting the eluted analyte composition; (5) simultaneously with each of steps (1)-(4), contacting each of the first waste composition, the second waste composition, and the eluted analyte composition with ultraviolet (UV) light, (6) measuring an absorbance of the UV light of each of the first waste composition, the second waste composition, and the eluted analyte composition to produce an absorbance value for each of the first waste composition, the second waste composition, and the eluted analyte composition; and (7) generating a chromatogram by plotting the absorbance value of each of the first waste composition, the second waste composition, and the eluted analyte composition as a function of volume of liquid that traverses the chromatography column.

In some embodiments of the methods of the disclosure, steps (a) or (b) generating a chromatogram comprise(s) a contacting step (5) and a measuring step (6), and furthermore, the contacting step (5) and measuring step (6) are continuous. In some embodiments, the contacting step (5) and measuring step (6) are simultaneous, sequential or alternating, and, continuous.

In some embodiments of the methods of the disclosure, the chromatography column comprises a matrix and the matrix comprises a resin.

In some embodiments of the methods of the disclosure, and in particular, with reference to steps (a) or (b) generating a chromatogram, test analyte is a biologic composition. In some embodiments, the biologic composition is a therapeutic composition for use in a method of treatment of a human subject. In some embodiments, the biologic composition comprises a therapeutic protein.

In some embodiments of the methods of the disclosure, the warning signal is communicated electronically to a processor and the processor is operably linked to the chromatography column. In some embodiments, the processor receives the warning signal and interrupts the chromatography process or prevents the initiation of a further chromatography process until the potential or actual malfunction of the chromatography column is resolved.

Additional aspects and embodiments of the invention will be apparent from the detailed description that follows.

DETAILED DESCRIPTION

A successful timely identification of failure mode in protein chromatography operation, especially in large-scale manufacturing, can be challenging not only because the failure mode is specific to each unit operation associated with a program but also, in the absence of the compositions and methods of the disclosure, an automatic detection method is not readily available.

The disclosure provides a novel Watch system and method for failure mode detection. This new Watch system and method of chromatography column monitoring is intended to alert an operator if the column is not performing its intended function. The Watch systems and methods of the disclosure automatically monitors system signals at integral times to determine if the column is performing optimally. If the system fails to meet the acceptance criteria, a message is displayed to the operator instructing them to add the event to the quality management system and to allow for further investigation and potentially remediation. Monitored signals, significant signal intensity, and integral time windows are all empirically determined for each unique chromatography unit operation to be monitored.

Chromatography

The systems and methods of the disclosure may be used for preparative or analytical chromatography. In some embodiments, methods of the disclosure are used to purify proteins that may be used in a composition for the treatment of a disease. Especially for those methods involving preparatory chromatography for the large scale or high volume purification of a therapeutic protein, efficiency of the purification process is essential. The systems and methods of the disclosure may be used at any scale. However, they are particularly useful when a large number of preparations are in process and when a malfunctioning system (such as a chromatography column that is allowing valuable analyte to pass though the separation composition when it should be capturing it), results in loss of a valuable product and valuable production time. The systems and methods of the disclosure predict and detect a malfunction in a chromatography process in real-time and, as a result of having identified the malfunctioning process, enable the restoration of function and return to efficient and reliable purification before additional work is performed using the malfunctioning process.

The disclosure encompasses any form of chromatography. As a technique, chromatography is a method of separating components from a mixture. Separation is achieved though the portioning of a mobile phase and a stationary phase. As described herein, the starting compositions comprising a test analyte, optionally also for preparation, belong to the mobile phase. As described herein, separation compositions comprising a matrix belong to the stationary phase. Exemplary matrices of the disclosure may comprise any material having the ability to separate elements of the mobile phase based on chemical properties (charge) and/or physical properties (size).

As used in some embodiments of the disclosure, including methods of preparation of therapeutic proteins, chromatography processes may include, but are not limited to, column and planar chromatography. In some preferred embodiments, chromatography processes may include, but are not limited to, column chromatography.

Column Chromatography

The disclosure encompasses any form of column chromatography, including wet and dry methods. In a dry method, the separation composition comprises a dry matrix, which is subsequently contacted with a liquid starting composition, optimally, wetting the entire matrix and not permitting the matrix to dry until the end of the entire process. In a wet method, the separation composition comprises suspension or slurry of a matrix and an eluent, which is introduced into the column and, subsequently contacted with a liquid starting composition.

Ion Exchange Chromatography

In some embodiments of the disclosure, the separation composition may comprise any material having the ability to separate elements of the mobile phase based on charge. For example, the separation composition may comprise a matrix that reversibly binds a charged protein analyte from a starting composition. Thus, the separation matrix may be suitable for anion- or cation-exchange chromatography and may comprise a matrix having net negative or positive charge, respectively. In some embodiments of the disclosure, the separation composition comprises a matrix comprising sepharose or Q sepharose. In some embodiments of the disclosure, the chromatography column is a Q column.

Affinity Chromatography

In some embodiments of the disclosure, the separation composition may comprise any material having the ability to separate elements of the mobile phase based on specific interactions between binding partners including, but not limited to, antigen/antibody binding partners, enzyme/substrate binding partners, receptor/ligand binding partners, protein/protein binding partners, protein/nucleic acid binding partners, and nucleic acid/nucleic acid binding partners. For example, the separation composition may comprise a matrix that reversibly binds one partner of a binding partner (e.g. an analyte from a starting composition) by comprising the other partner of a binding partner. By way of example, the separation composition may comprise a matrix that comprises an antigen to which the analyte of the starting composition specifically binds to selectively purify the antibody analyte from the starting material. By way of further illustration, the separation composition may comprise a matrix that comprises an epitope of a VEGF protein to which a VEGF-Trap selectively binds to selectively purify the VEGF-Trap analyte from the starting material.

Hydrophobic Interaction Chromatography (HIC)

In some embodiments of the disclosure, the separation composition may comprise any material having the ability to separate elements of the mobile phase based on their relative hydrophobicity. HIC may be used to selectively purify a protein analyte while maintaining its biological activity as a result of the use of conditions and of matrices that operate under less denaturing conditions. In some embodiments, analytes of the disclosure containing hydrophobic and hydrophilic regions are contacted to an HIC column in a high-salt buffer. The salt in the buffer reduces the solvation of analyte solutes in the starting material. As solvation decreases, hydrophobic regions that become exposed are adsorbed by the media. The more hydrophobic the molecule in the starting material, the less salt is needed to promote binding. A decreasing salt gradient may be used to elute samples from the column in order of increasing hydrophobicity. Elution buffers of the disclosure may also comprise a mild organic modifier or a mild detergent.

Size Exclusion Chromatography (SEC)

In some embodiments of the disclosure, the separation composition may comprise any material having the ability to separate elements of the mobile phase based on their relative size, or in some cases, relative molecular weights. SEC may be used to selectively purify large molecules or macromolecular complexes such as proteins and polymers. In some embodiments, for example those embodiments wherein an aqueous solution is used to transport the mobile phase through the column, the technique is known as gel-filtration chromatography. In some embodiments, for example those embodiments wherein an organic solvent is used as a mobile phase through the column, the technique is known as gel permeation chromatography. In some embodiments, the chromatography column is packed with fine, porous beads which are composed of, for example, dextran polymers (Sephadex), agarose (Sepharose), or polyacrylamide (Sephacryl or BioGel P). The pore sizes of these beads are used to estimate the dimensions of macromolecules. Gel-filtration chromatography can be used to fractionate protein analytes and other water-soluble polymers, while gel permeation chromatography can be used to fractionate organic-soluble polymers based on molecular weight distribution.

High Performance Liquid Chromatography (HPLC)

In some embodiments of the disclosure, the separation composition may comprise any material having the ability to separate elements of the mobile phase based on their interaction with the adsorbent material of the separation composition, which causes different flow rates for the different components and leads to the separation of the components as they flow out of the column. Analytes in the mobile phase can be separated, for example, through hydrophobic, ionic or dipole-dipole interactions. HPLC relies on pumps to pass a pressurized liquid solvent containing the mobile phase through a column filled with a solid adsorbent material. In some embodiments, the active component of the column, the adsorbent comprises a granular material made of solid particles (for example, silica or polymers). Exemplary particle sizes include 2-50 micron particles, which small size can give HPLC chromatography superior resolving power. In some embodiments, the pressurized mobile phase is a mixture of solvents, such as water, acetonitrile and/or methanol. In some embodiments, an HPLC pump mixes multiple solvents together in ratios changing in time, generating a gradient composition in the mobile phase. In some embodiments, the aqueous component of the mobile phase contains acids (such as formic, phosphoric or trifluoroacetic acid) or salts to assist in the separation of the sample components. In some embodiments, the HPLC comprises partition chromatography, normal-phase chromatography, displacement chromatography, reversed-phase chromatography, size exclusion chromatography, ion-exchange chromatography, affinity chromatography, hydrophobic interaction chromatography or aqueous normal-phase chromatography.

Fast Protein Liquid Chromatography (FPLC)

In some embodiments of the disclosure, the separation composition may comprise any material having the ability to separate elements of the mobile phase based on their different affinities for the separation composition. Fast protein liquid chromatography (FPLC) is a form of liquid chromatography that is used to separate mixtures of protein analytes. In some embodiments, separation is possible because the different components of a mobile phase have different affinities for mobile phase and the stationary phase (the separation composition). In some embodiments, the mobile phase is an aqueous solution, or buffer. The buffer flow rate can be controlled by a positive-displacement pump. In some embodiments, the buffer flow rate is constant, and the composition of the buffer is varied. In some embodiments, the stationary phase is a resin composed of beads, for example agarose beads. The person of ordinary skill will be able to vary bead sizes and surface ligands of the stationary phase depending upon the mobile phase and analytes of a particular application.

In some embodiments, the FPLC comprises ion exchange chromatography. For example, a stationary phase resin binds a protein analyte by a charge interaction while in a first buffer (the running buffer), but dissociates in a second buffer (the elution buffer). A mixture containing one or more protein analytes is dissolved in the first buffer and pumped into the column. The proteins of interest bind to the resin while other components are carried out in the first buffer. The total flow rate of the buffer is kept constant. Over time, the percentage of the elution buffer is gradually increased from 0% to 100% according to a programmed change in concentration to produce a gradient. At some point along the gradient each of the bound protein analytes dissociates and appears in the eluate. The eluate then passes through detectors. Exemplary detectors can measure salt concentration of the eluate (by conductivity) and protein concentration of the eluate (by absorption of ultraviolet light).

Pressurization

In some embodiments of the methods of the disclosure, flow of the mobile phase through the stationary phase is controlled by gravity. In some embodiments, gravity chromatography is used for single-step purifications like desalting and affinity applications. A typical gravity column comprises a top buffer reservoir element operably linked to a chromatography column with an outlet at the bottom. Flow is controlled using a stopcock or a tubing pincher between the buffer reservoir and the column. Flow adaptors can be used to minimize variability in sample loading. In some embodiments, the gravity chromatography comprises partition chromatography, normal-phase chromatography, displacement chromatography, reversed-phase chromatography, size exclusion chromatography, ion-exchange chromatography, affinity chromatography, hydrophobic interaction chromatography or aqueous normal-phase chromatography.

In some embodiments of the methods of the disclosure, the chromatography comprises low pressure chromatography. In some embodiments, a low pressure chromatography system is a system that operates at pressures of less than 50 psi (~3 bar). Low-pressure chromatography can be used protein separations that do not require high resolution.

In some embodiments of the methods of the disclosure, the chromatography comprises medium pressure chromatography. In some embodiments, a medium pressure chromatography system is a system that operates at pressures of up to 3,500 psi (24 Mpa). Medium-pressure chromatography systems produce enough pressure to accommodate higher resolution stationary phase compositions, for example using 5-15 μm beads. In some embodiments, the medium pressure chromatography comprises partition chromatography, normal-phase chromatography, displacement chromatography, reversed-phase chromatography, size exclusion chromatography, ion-exchange chromatography, affinity chromatography, hydrophobic interaction chromatography or aqueous normal-phase chromatography.

In some embodiments of the methods of the disclosure, the chromatography comprises high pressure chromatography, for example HPLC.

Mobile Phase

The disclosure encompasses any form of mobile phase, including, but not limited to, an eluent, a solvent, a sterile solvent, and a pharmaceutically-acceptable carrier. Elution compositions of the disclosure may comprise a pharmaceutically-acceptable carrier.

Stationary Phase

The disclosure encompasses any form of stationary phase, including, but not limited to, silica, alumina ($Al_2O_3$), cellulose, sepharose and Q sepharose. Exemplary separation compositions of the disclosure may comprise, a matrix, a polymer, a resin, a protein, or a combination thereof. In some embodiments, the separation composition comprises sepharose or Q sepharose.

Chromatograms

As used herein, a chromatogram is the visual output of a chromatograph. Typically, retention time and/or outflow volume of the eluate are represented on the x axis of the chromatogram, and a signal is plotted on the y axis. Exemplary signals include, but are not limited to electrical conductance, light absorbance and mass spectrometry, and correspond to a response of a detector to analytes exiting the chromatograph. In some embodiments, this signal is proportional to the concentration of a specific analyte being separated by the chromatograph.

In one exemplary embodiment, protein concentration, as measured by light absorption, is plotted on they y axis of the chromatogram. Many proteins in solution absorb light, for example ultraviolet light at a wavelength of 280 nm, which can be used to calculate protein concentration in a sample. Depending on the protein, additional wavelengths of light are contemplated. For example, proteins comprising heme groups or fluorophores will be detectable with different wavelengths of light. The person of ordinary skill will be able to select a suitable detection system for a specific analyte.

Biological Samples

In some embodiments of the methods of the disclosure, the analyte comprises a protein, a peptide, a nucleic acid or a virus. In some embodiments, the nucleic acid is deoxyribonucleic acid (DNA) or ribonucleic acid (RNA). In some embodiments, the virus is an adenovirus, an adeno-associated virus or a lentivirus.

EXAMPLES

Example 1: Purification of a VEGF Trap

Figure 1:
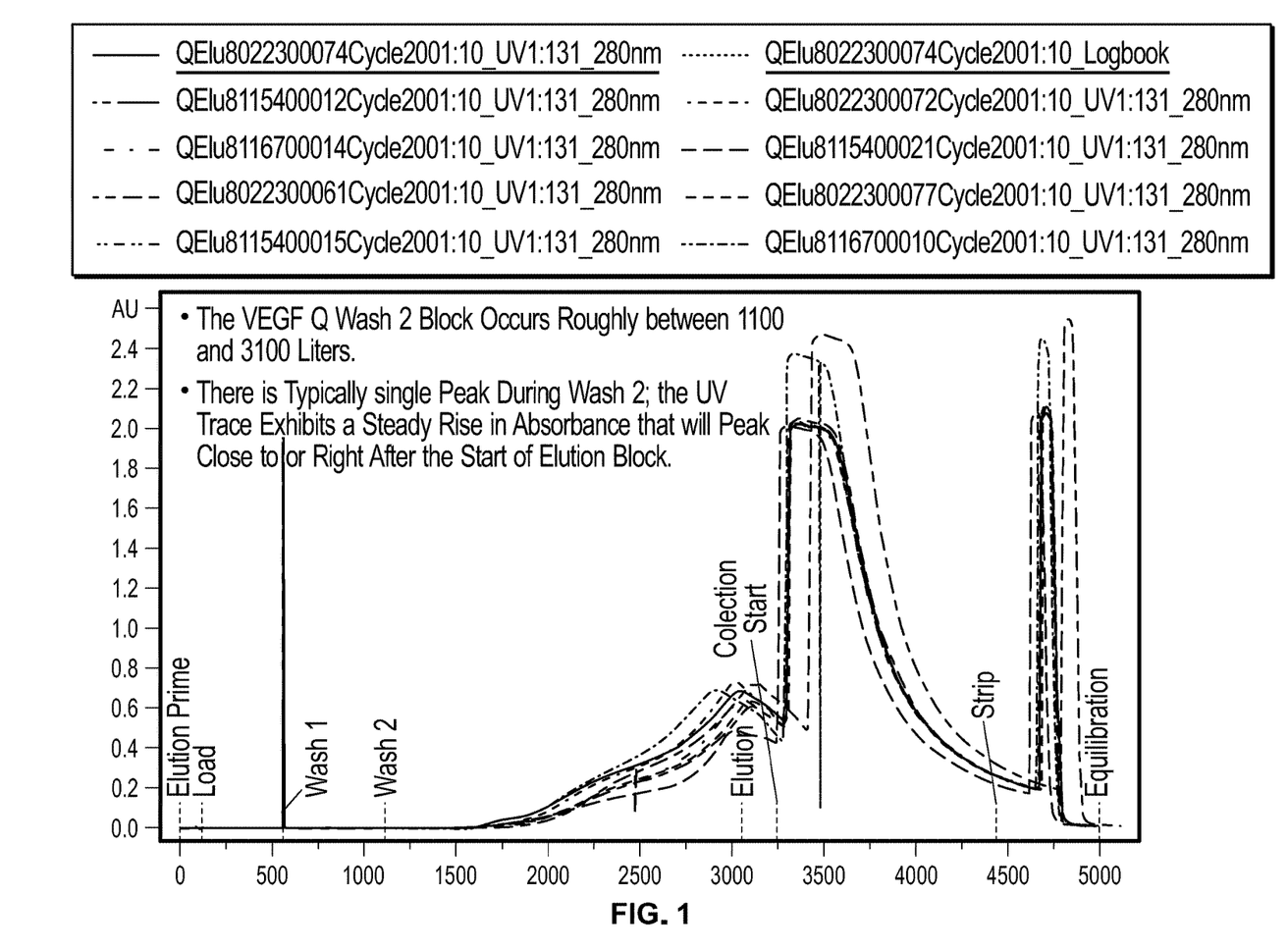
FIG. 1 represents the reference chromatograms, that is the historical norm.
Figure 2:
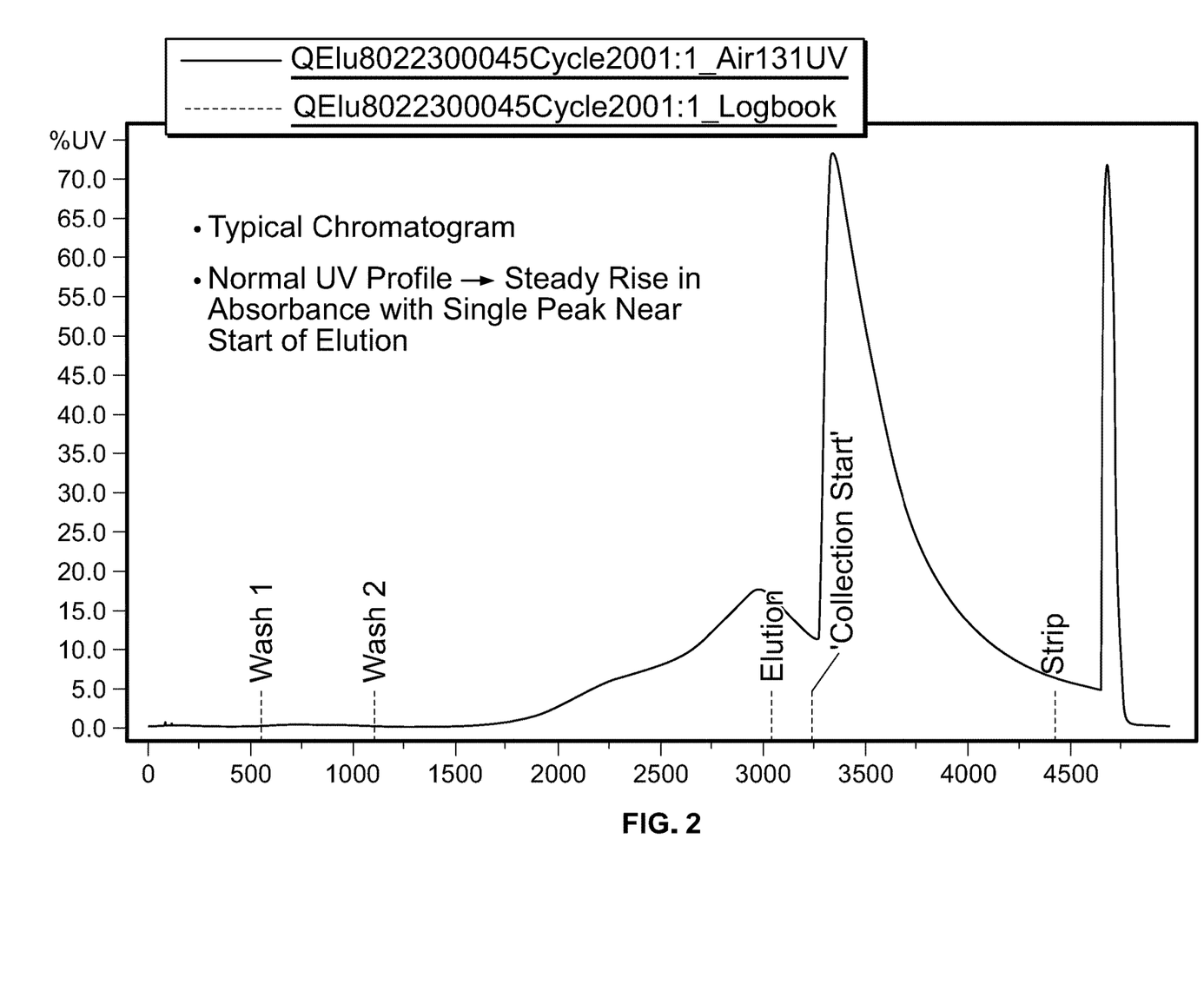
FIG. 2 represents another reference chromatogram.
Figure 3:
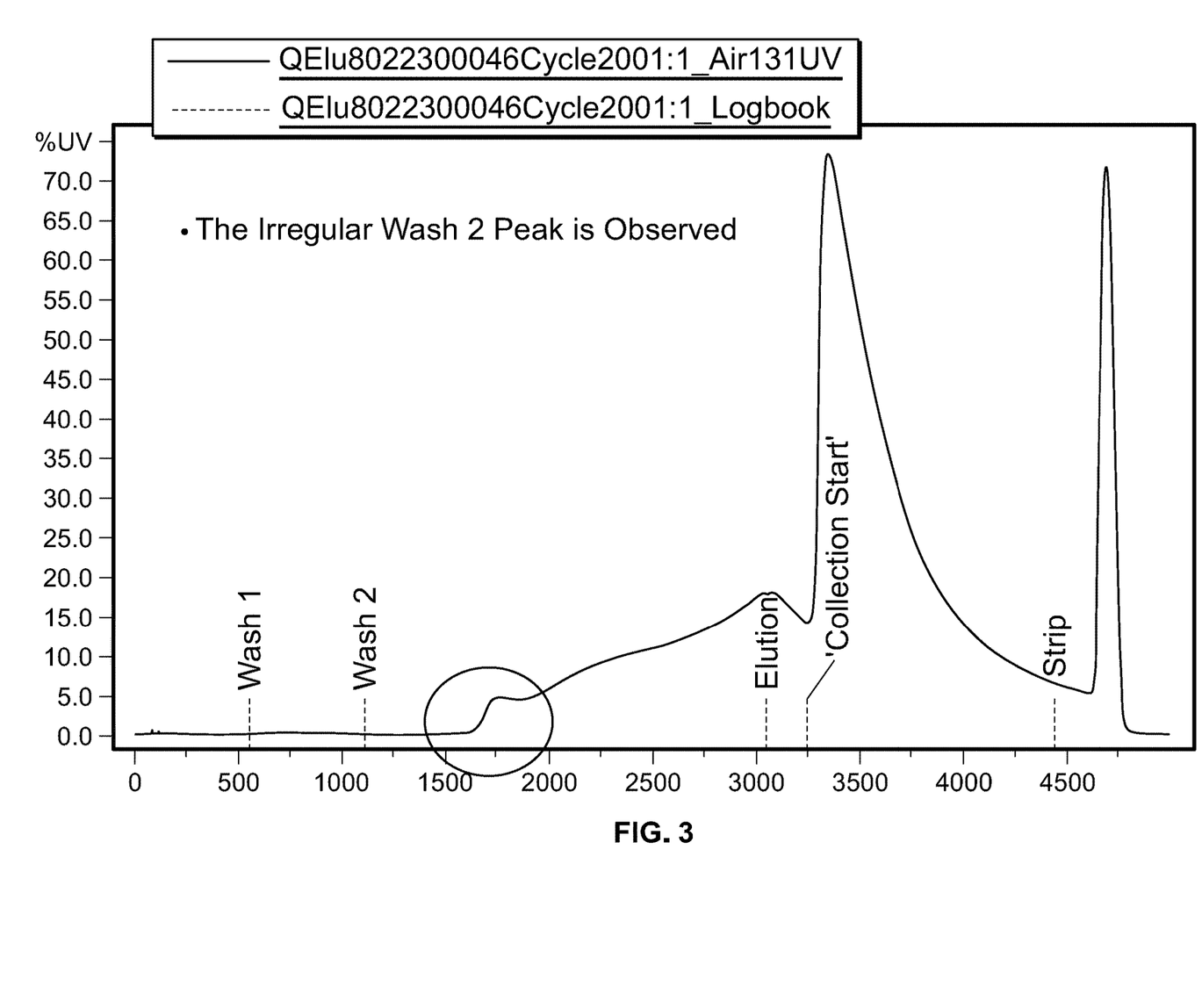
FIG. 3 represents a chromatogram displaying an irregular Wash 2 peak.
Figure 4:
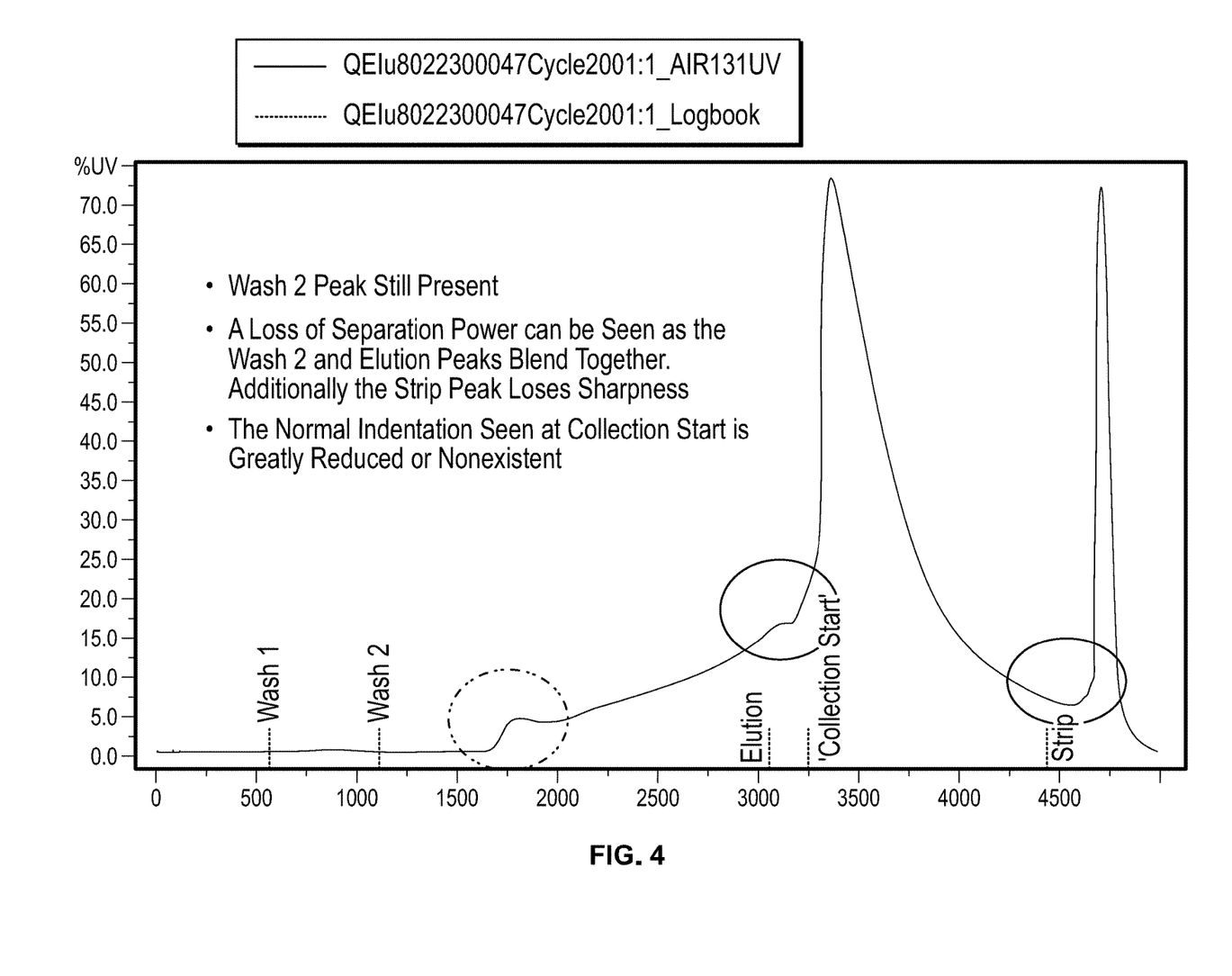
FIG. 4 represent a chromatogram displaying an irregular Wash 2 peak, irregular elution peaks, and loss of sharpness in the Strip peak.
Figure 5:
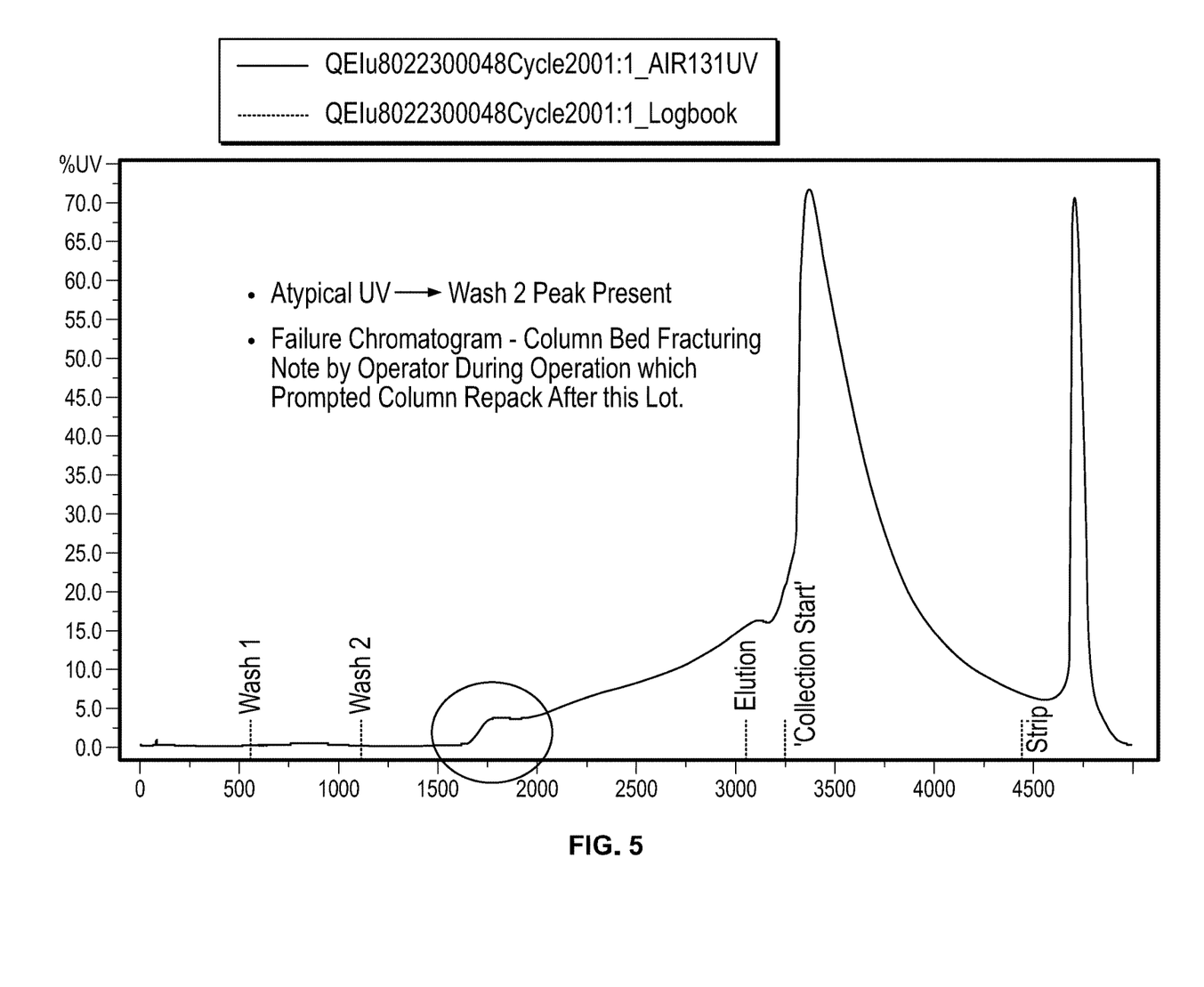
FIG. 5 represents a failure chromatogram. The Wash 2 peak is present.
Figure 6:
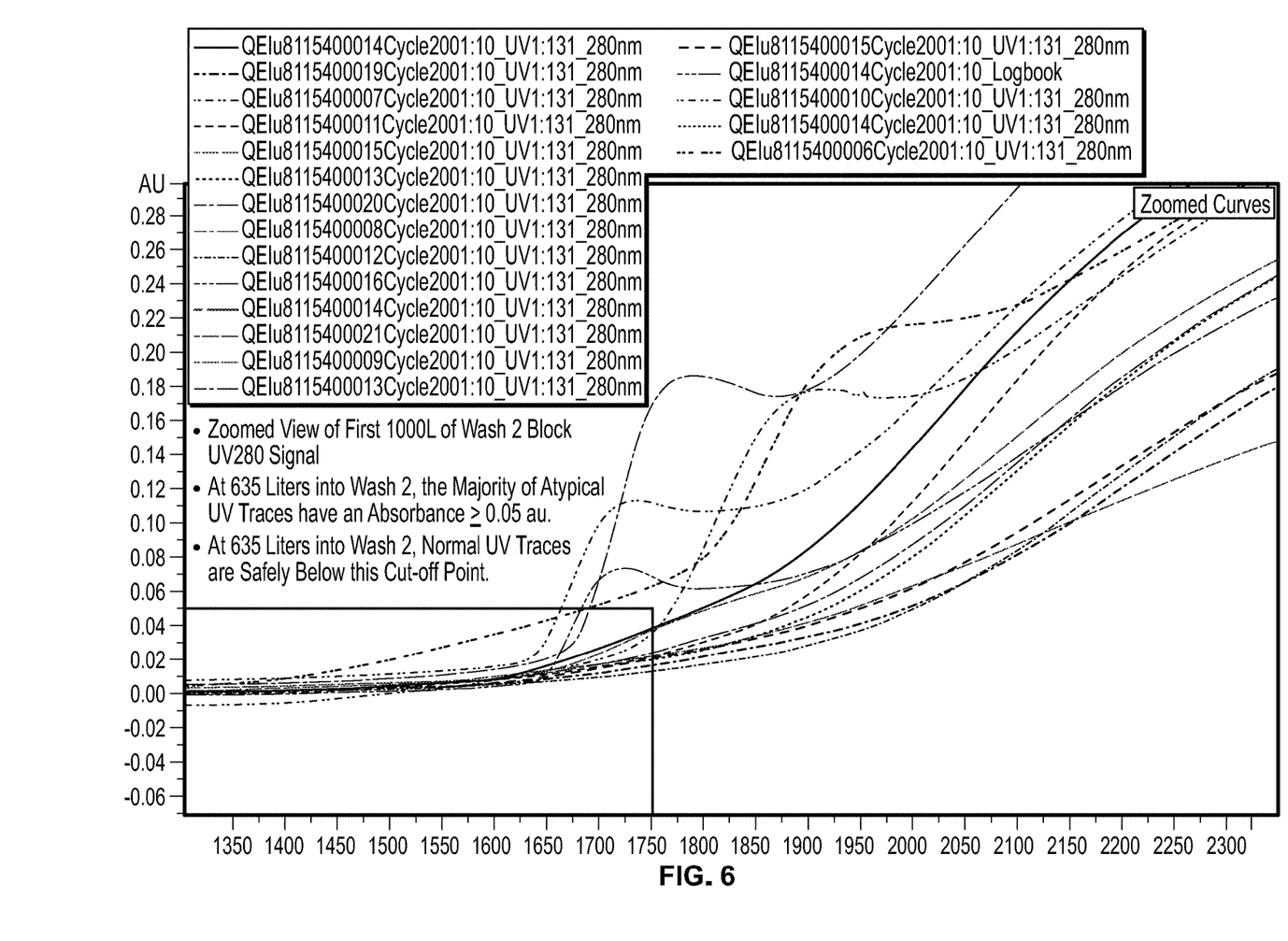
FIG. 6 represents comparison of typical and atypical VEGF-Trap Q chromatograms. The majority of atypical UV traces have an absorbance ≥0.05 au at 635 liters into Wash 2.
Figure 7:
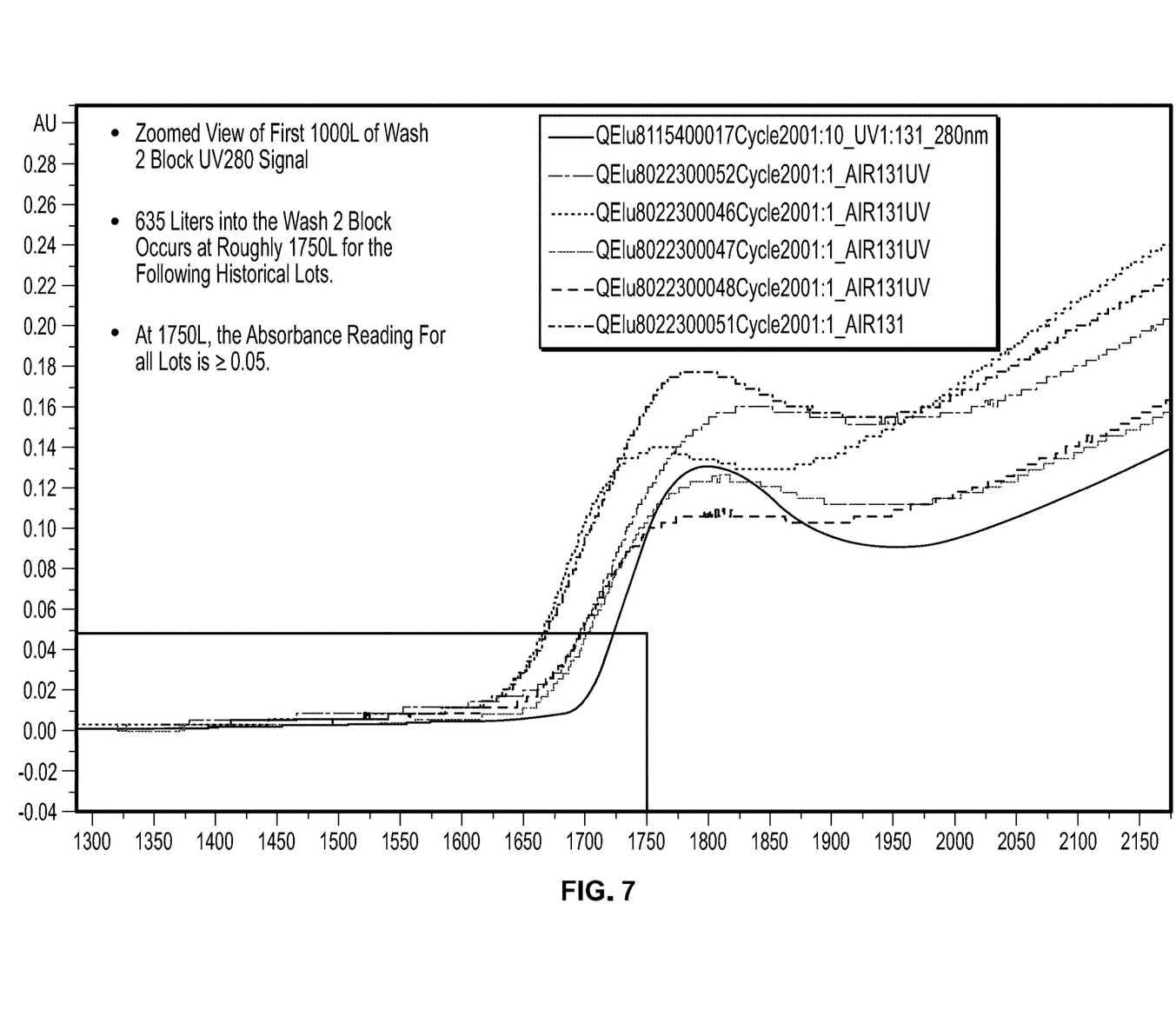
FIG. 7 represents additional atypical VEGF-Trap Q chromatograms, that is, Wash 2 peak examples.
Figure 8:
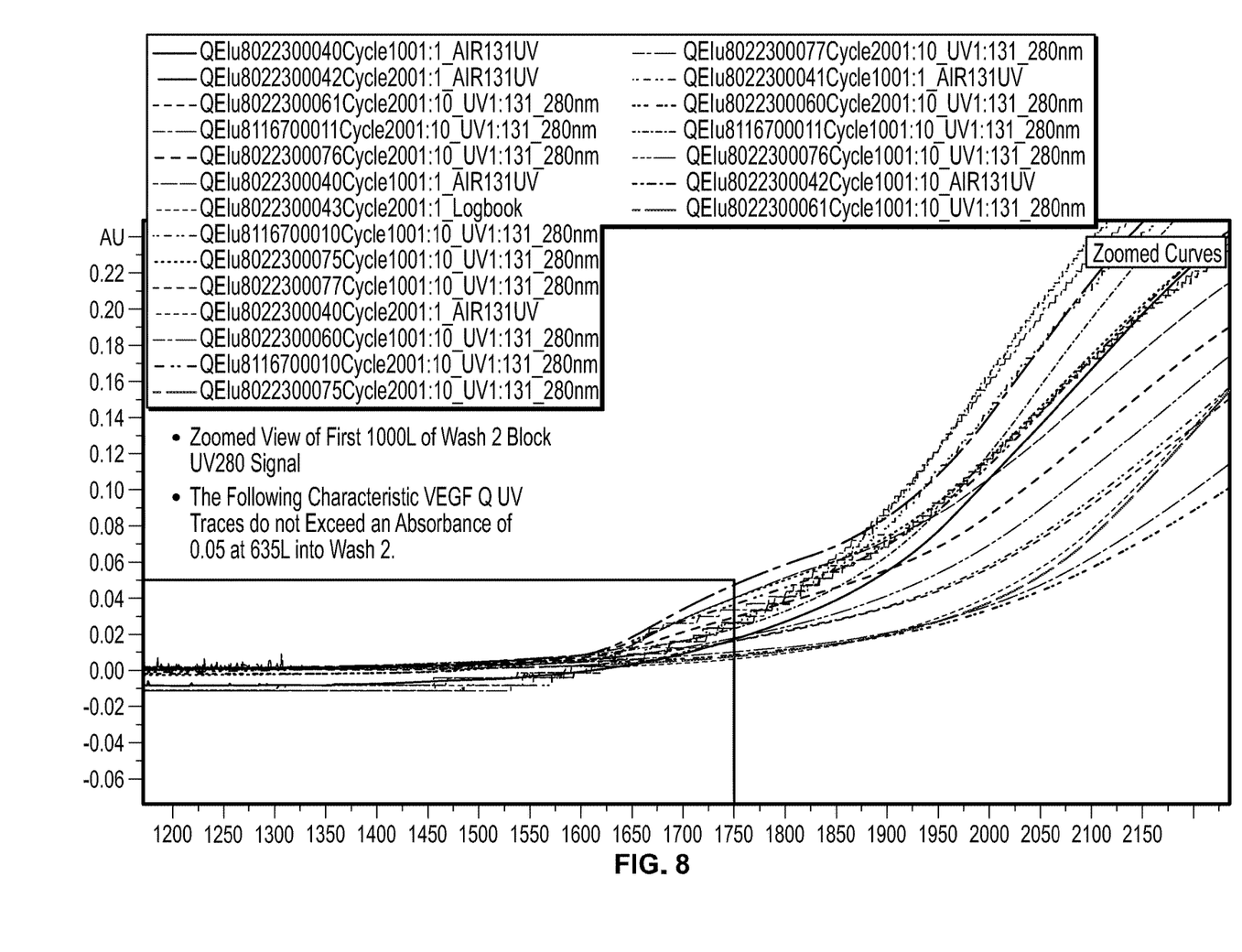
FIG. 8 represents additional typical VEGF-Trap Q chromatograms. UV traces do not exceed an absorbance of 0.05 at 635 liters into Wash 2.

Using a VEGF-Trap as an exemplary analyte for purification, FIGS. 1-8 depict both exemplary reference chromatograms (FIGS. 1 and 2) as well as exemplary process chromatograms having an atypical profile (FIGS. 3 through 5).

Briefly, the chromatograms of FIGS. 1-8 where generated by contacting a starting composition comprising a plurality of analytes (VEGF-Trap analytes as well as a plurality of contaminants (e.g. host cell proteins, DNA and poorly sialiated proteins)) and a separation composition comprising a matrix (in this example, Q Sepharose), under conditions sufficient for at least one VEGF-Trap protein of the starting composition to reversibly bind to the matrix, wherein the chromatography column comprises the separation composition, to produce an analyte-bound column and a first waste composition. Next, the analyte-bound column and a first washing composition were contacted, wherein the VEGF-Trap protein of the starting composition remains bound to the matrix to produce a purified analyte-bound column and a second waste composition. The analyte-bound column and a second washing composition were contacted, wherein, in the reference chromatogram depicting a typical profile, the VEGF-Trap protein of the starting composition remains bound to the matrix to produce a purified analyte-bound column and a third waste composition. To generate the process chromatograph depicting an atypical profile, the analyte-bound column and a second washing composition were contacted, wherein, in the process chromatogram depicting an atypical profile, only the VEGF-Trap protein of the starting composition remains bound to the matrix to produce a purified analyte-bound column and a third waste composition, however, the third waste composition comprises a contaminant or a VEGF-Trap protein. In both the reference and process chromatograms, the purified analyte-bound column and an elution composition are contacted, wherein the at least one analyte of the starting composition is released from the matrix into the elution composition to produce an eluted analyte composition. In both the reference and process chromatograms, the eluted analyte composition is collected. Simultaneously with each of above, each of the first waste composition, the second waste composition, the third waste composition and the eluted analyte composition are contacted with ultraviolet (UV) light. Simultaneously or sequentially, an absorbance of the UV light of each of the first waste composition, the second waste composition, the third waste composition and the eluted analyte composition is measured to produce an absorbance value for each of the first waste composition, the second waste composition, the third waste composition, and the eluted analyte composition. The absorbance values for each of the first waste composition, the second waste composition, the third waste composition and the eluted analyte composition were plotted as a function of volume of liquid that traverses the chromatography column to generate a chromatogram. Generation of the chromatograph occurs in real-time with the chromatography process and the occurrence of an atypical profile is determined as the additional peak appears on the chromatogram. The appearance of an atypical profile causes a detector and/or a processor to send a warning signal to a processor operably-linked to the chromatography column, which, in turn, prevents a subsequent chromatography process until the malfunction of the column can be resolved.

What is claimed:

1. A method for detecting a column malfunction in a chromatography process, comprising:
    (a) contacting a reference sample comprising a plurality of analytes and a biologic composition with a chromatography column comprising a separation composition comprising a matrix, under conditions sufficient for the biologic composition to reversibly bind to and be eluted from the matrix upon contacting the matrix with an elution composition, whereby generating a reference chromatogram from the chromatography column by plotting an absorbance value of at least a first waste composition, a second waste composition and an eluted analyte composition as a function of volume of liquid that traverses the chromatography column, wherein the plotting occurs continuously as the compositions exit the chromatography column;
    (b) contacting a process sample comprising the plurality of analytes and the biologic composition with a chromatography column comprising a separation composition comprising a matrix, under conditions sufficient for the biologic composition to reversibly bind to and be eluted from the matrix upon contacting the matrix with the elution composition, whereby generating a process chromatogram from the chromatography column by plotting an absorbance value of at least a first waste composition as a function of volume of liquid that traverses the chromatography column, wherein the plotting occurs continuously as the composition exits the chromatography column;
    (c) comparing the process chromatogram to the reference chromatogram thereby detecting an atypical profile in the process chromatogram, wherein the atypical profile comprises one or more features which indicate the column malfunction selected from the group consisting of:
    an additional peak on the process chromatogram when compared to a comparable position on the reference chromatogram,
    and
    a measured absorbance intensity exceeding a maximum absorbance intensity during an integral volume window,
        wherein the one or more features, which indicate the column malfunction, occur prior to a step of contacting the chromatography column with an elution composition;
    (d) generating a warning signal when the atypical profile is detected; and
    (e) halting the chromatography process when the atypical profile is detected and until the column malfunction is resolved.

2. The method of claim 1, wherein the chromatography process comprises ion exchange chromatography.

3. The method of claim 1, wherein the chromatography process comprises affinity chromatography.

4. The method of claim 1, wherein the chromatography process comprises hydrophobic interaction chromatography.

5. The method of claim 1, wherein the column malfunction is caused by column deterioration.

6. The method of claim 5, wherein the column deterioration comprises column bed fracturing.

7. The method of claim 1, wherein the additional peak occurs during a washing step in the chromatography process.

8. The method of claim 1, wherein the magnitude of the additional peak indicates a degree of severity of the column malfunction.

9. The method of claim 8, wherein an increase in the magnitude of the additional peak indicates an increase in the degree of severity of the column malfunction of the chromatography process.

10. The method of claim 1, wherein the column malfunction induces a loss of separation power of the chromatography column.

11. The method of claim 1, wherein the measured absorbance intensity is determined at a wavelength corresponding to ultraviolet (UV) light.

12. The method of claim 11, wherein the measured absorbance intensity is determined at a wavelength of between 260 nanometers (nm) and 280 nm, inclusive of the endpoints.

13. The method of claim 11, wherein the measured absorbance intensity is determined at a wavelength of 260 nm, providing an $A_{260}$ value.

14. The method of claim 11, wherein the measured absorbance intensity is determined at a wavelength of 280 nm, providing an $A_{280}$ value.

15. The method of claim 13, wherein the maximum absorbance intensity has an $A_{260}$ value or an $A_{280}$ value of at least 0.05.

16. The method of claim 1, wherein the reference chromatogram comprises a measured absorbance intensity that does not exceed a maximum absorbance intensity during an integral volume window and wherein the maximum absorbance intensity has an $A_{260}$ value or an $A_{280}$ value of 0.05 or less.

17. The method of claim 1, wherein the integral volume window occurs between 1000 L and 2500 L, inclusive of the endpoints.

18. The method of claim 17, wherein the integral volume window occurs between 1250 L and 2250 L, inclusive of the endpoints.

19. The method of claim 17, wherein the integral volume window occurs between 1600 L and 1800 L, inclusive of the endpoints.

20. The method of claim 1, wherein the chromatography column comprises an anion exchange resin.

21. The method of claim 1, wherein the step of (a) generating the reference chromatogram comprises:
    (1) binding the biologic composition to the matrix, to produce a biologic composition bound column and a first waste composition;
    (2) contacting the biologic composition bound column of (1) and a washing composition, wherein the biologic composition remains bound to the matrix to produce a purified biologic composition bound column and a second waste composition;

(3) contacting the purified biologic composition bound column of (2) and an elution composition, wherein the biologic composition is released from the matrix into the elution composition to produce an eluted biologic composition;

(4) collecting the eluted biologic composition;

(5) simultaneously with each of steps (1)-(4), contacting each of the first waste composition, the second waste composition, and the eluted biologic composition with ultraviolet (UV) light, (6) measuring an absorbance of the UV light of each of the first waste composition, the second waste composition, and the eluted biologic composition to produce an absorbance value for each of the first waste composition, the second waste composition, and the eluted biologic composition; and (7) generating a chromatogram by plotting the absorbance value of each of the first waste composition, the second waste composition, and the eluted biologic composition as a function of volume of liquid that traverses the chromatography column.

22. The method of claim 21, wherein the contacting step (5) and measuring step (6) are continuous.

23. The method of claim 21, wherein the matrix comprises a resin.

24. The method of claim 21, wherein the biologic composition is a therapeutic composition for use in a method of treatment of a human subject.

25. The method of claim 1, wherein the warning signal is communicated electronically to a processor and wherein the processor is operably linked to the chromatography column.

26. The method of claim 25, wherein the processor receives the warning signal and interrupts the chromatography process or prevents the initiation of a further chromatography process until the column malfunction is resolved.

27. The method of claim 1, wherein resolving the column malfunction comprises repacking the chromatography column.

28. The method of claim 1, wherein the biologic composition comprises a therapeutic protein.

29. The method of claim 28, wherein the therapeutic protein in the reference sample is the same or substantially similar to the therapeutic protein in the process sample.

30. The method of claim 1, wherein the biologic composition comprises a VEGF-Trap protein.

31. The method of claim 1, wherein the step of (b) generating the process chromatogram comprises:

(1) binding the biologic composition to the matrix, to produce a biologic composition bound column and a first waste composition;

(2) contacting the biologic composition bound column of (1) and a washing composition, wherein the biologic composition remains bound to the matrix to produce a purified biologic composition bound column and a second waste composition;

(3) contacting the purified biologic composition bound column of (2) and an elution composition, wherein the biologic composition is released from the matrix into the elution composition to produce an eluted biologic composition;

(4) collecting the eluted biologic composition;

(5) simultaneously with each of steps (1)-(4), contacting each of the first waste composition, the second waste composition, and the eluted biologic composition with ultraviolet (UV) light, (6) measuring an absorbance of the UV light of each of the first waste composition, the second waste composition, and the eluted biologic composition to produce an absorbance value for each of the first waste composition, the second waste composition, and the eluted biologic composition; and (7) generating a chromatogram by plotting the absorbance value of each of the first waste composition, the second waste composition, and the eluted biologic composition as a function of volume of liquid that traverses the chromatography column wherein generating the process chromatogram occurs simultaneously with contacting each of the first waste composition, the second waste composition, and the eluted biologic composition with ultraviolet (UV) light, and wherein the chromatography process is interrupted prior to step (3) upon detection of an atypical profile until the column malfunction is resolved.

* * * * *